(12) United States Patent
Chen et al.

(10) Patent No.: US 8,983,033 B2
(45) Date of Patent: Mar. 17, 2015

(54) SCANNING DEVICE AND METHOD FOR BACK-SCATTER IMAGING WITH A RADIATION BEAM

(75) Inventors: Zhiqiang Chen, Beijing (CN); Yuanjing Li, Beijing (CN); Ziran Zhao, Beijing (CN); Yinong Liu, Beijing (CN); Wanlong Wu, Beijing (CN); Li Zhang, Beijing (CN); Chao Tu, Beijing (CN); Le Tang, Beijing (CN); Yingkang Jin, Beijing (CN); Shuo Cao, Beijing (CN); Guangwei Ding, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 931 days.

(21) Appl. No.: 13/142,668

(22) PCT Filed: Apr. 28, 2011

(86) PCT No.: PCT/CN2011/073474
§ 371 (c)(1),
(2), (4) Date: Jun. 29, 2011

(87) PCT Pub. No.: WO2012/088810
PCT Pub. Date: Jul. 5, 2012

(65) Prior Publication Data
US 2012/0170716 A1    Jul. 5, 2012

(30) Foreign Application Priority Data
Dec. 31, 2010  (CN) .......................... 2010 1 0624252

(51) Int. Cl.
   *G01N 23/203*    (2006.01)
(52) U.S. Cl.
   CPC ................................ *G01N 23/203* (2013.01)
   USPC .......................................................... 378/87
(58) Field of Classification Search
   USPC ............ 378/87, 57, 145–147, 150–152, 101, 378/106
   See application file for complete search history.

(56) References Cited

U.S. PATENT DOCUMENTS

| 4,342,914 A | 8/1982 | Bjorkholm ...................... 378/99 |
| 4,745,631 A | 5/1988 | Paolini |

(Continued)

FOREIGN PATENT DOCUMENTS

| CN | 1246647 A | 3/2000 |
| CN | 201173903 Y | 12/2008 |

(Continued)

OTHER PUBLICATIONS

Second Chinese Office Action for Chinese Patent Application No. 201010624252.3, dated Dec. 24, 2013, 8 pages.
Communication including extended European Search Report for European Patent Application No. 11778783.8-1554/2573551, dated Mar. 25, 2014, 9 pages.    (Continued)

*Primary Examiner* — Irakli Kiknadze
(74) *Attorney, Agent, or Firm* — Westman, Champlin & Koehler, P.A.

(57) ABSTRACT

The present invention discloses a scanning device of back-scatter imaging with a radiation beam, comprising: a radiation source; a fixed shield plate and a rotatable shield body disposed between the radiation source and a object to be scanned respectively, wherein the fixed shield plate is stationary with respect to the radiation source and the rotatable shield body is rotatable with respect to the fixed shield plate. The fixed shield plate is provided with a ray passing-through region thereon, which allows for a radiation beam from the radiation source to pass through the fixed shield plate, a ray incidence region and a ray emergence region are arranged on the rotatable shield body respectively, during the rotatable scanning of the rotatable shield body, the ray passing-through region of the fixed shield plate continuously intersects with the ray incidence region and the ray emergence region of the rotatable shield body to generate collimated holes for scanning. The ray passing-through region of the fixed shield plate is a rectilinear slit, the rotatable shield body is a cylinder, and the ray incidence and emergence regions are configured to be a series of small discrete holes disposed along a spiral line respectively. In addition, the present invention discloses a scanning method for back-scatter imaging with a radiation beam.

10 Claims, 5 Drawing Sheets

(56) References Cited

U.S. PATENT DOCUMENTS

| | | | |
|---|---|---|---|
| 5,493,596 A * | 2/1996 | Annis | 378/57 |
| 6,272,206 B1 | 8/2001 | Bjorkholm | 378/146 |
| 2007/0172031 A1 | 7/2007 | Cason et al. | |

FOREIGN PATENT DOCUMENTS

| | | |
|---|---|---|
| CN | 201285377 Y | 8/2009 |
| CN | 101644687 A | 2/2010 |
| CN | 202013328 U | 10/2011 |
| EP | 0389033 A2 | 9/1990 |
| JP | 1989147351 A | 6/1989 |
| JP | 2003514245 A | 4/2003 |
| WO | 01/37287 A1 | 5/2001 |

OTHER PUBLICATIONS

Office Action for Chinese Patent Application No. 201010624252.3, dated Apr. 16, 2013, 8 pages.

Search Report and Written Opinion from PCT Application No. PCT/CN2011/073474, dated Oct. 13, 2011, 8 pgs.

First Japanese Office Action for Japanese patent application No. 2013-545014, dated May 27, 2014, 4 pages.

Third Chinese Office Action for Chinese patent application No. 201010624252.3, dated Jun. 12, 2014, 8 pages.

Official Action for Ukrainian patent application No. 2013 07518, dated Apr. 7, 2014, 7 pages.

Examination Report for Australian patent application No. 2011349928, dated May 2, 2014, 3 pages.

* cited by examiner

SCANNING DEVICE AND METHOD FOR BACK-SCATTER IMAGING WITH A RADIATION BEAM

CROSS-REFERENCE TO RELATED APPLICATION

This application is a Section 371 National Stage Application of International Application No. PCT/CN2011/073474, filed Apr. 28, 2011 and not yet published, which claims the benefit of Chinese Patent Application No. 201010624252.3 filed on Dec. 31, 2010 in the State Intellectual Property Office of China, the disclosure of which is incorporated herein by reference.

BACKGROUND OF THE INVENTION

1. Field of the Invention

The present invention relates to a field of application of nuclear technique, more particularly, to a non-destructive detecting device and method for human and object. In general, it relates to a scanning device and method for imaging with back-scatter radiation beam.

2. Description of the Related Art

In the field of non-destructive detection and human body detection, there are two types of imaging approaches with radiation rays: transmission imaging and back-scatter imaging. The principle of the back-scatter imaging is that the object is scanned by a radiation beam, and at the same time scattering signals scattered from the object to be scanned are received by a detector. During the subsequent data processing step, the scanning positions are correlated to the scattering signals one by one, and thereby obtaining the scattering image about the object to be scanned. The key component in the back-scatter imaging system is a flying spot scanning mechanism which collimates ray so as to carry out two-dimensional scanning.

In a flying spot scanning mechanism in the prior art, a rotatable shield body with a plurality of collimated holes is employed to perform an one dimensional scan (referred as a first dimensional scan) by rotating it within a ray scanning sector, and to perform another dimensional scan (referred as a second dimensional scan) by rotating or translating the ray scanning sector. As for the first dimensional scan, ray is scanned in a non-uniform velocity over a vertical plane of the object, the scanning line is accelerated at both leading and trailing ends when scanning. Further, the scanning spot is further longitudinally enlarged on the basis of the geometry deformation, so that the image has a longitudinally compressive deformation due to the change of the scanning speed in addition to the geometry deformation.

When performing the second dimensional scan through translating the ray scanning sector, it is necessary to translate a ray generator and the rotatable shield body. As a result, the construction and configuration of the scanning device become rather complicated. On the other hand, if ray scanning sector is rotated during scanning operation, it is required to overcome rotational inertia for rotating the shield body. Meanwhile, it imposes enormous impact and pressure on the driving device for rotating the shield body and a bearing structure for bearing the shield body when the rotation operation is carried out.

Another known flying spot scanning mechanism comprises a fixed shield plate located at front of a ray source and a rotatable shield body. The fixed shield plate is stationary with respect to the ray source, and the rotatable shield body is rotatable with respect to the fixed shield plate. The fixed shield plate is provided with a rectilinear slit while the rotatable shield body is provided with a spiral slit, respectively. Upon performing scanning through rotating the rotatable shield body, the rectilinear slit continually intersects with the spiral slit to generate collimated holes for scanning which always keep a predetermined shape with respect to the ray source, so that a sectional shape of the radiation beam passing through the collimated hole for scanning is kept to be constant.

In the above configuration, since the spiral slit is arranged on the rotatable shield body, it is easy to control the shape and size of the collimated hole for scanning. Meanwhile, it is necessary to further improve and enhance shielding of the radiation rays.

Furthermore, since the rotatable shield body is required to be precisely machined to have the spiral slit, which engenders problems and rigorous requirements on manufacturing the rotatable shield body.

Moreover, the rotatable shield body is required to rotate during the scanning, thereby giving rise to a problem that the weight and rotatable inertia of the scanning should be taken into accounts.

Accordingly, it is desirable to provide a novel scanning device for back-scatter imaging with the radiation beam, which can meet at least one aspect of the above requirements or demands.

SUMMARY OF THE INVENTION

Bearing in mind of the above shortages in prior arts, an object of the present invention is to alleviate at least one aspect of the above problems and defects.

Accordingly, one object of the present invention is to provide an improved scanning device and method for imaging with back-scatter radiation beam, wherein shape and size of the collimated hole for scanning can be used to provide a uniform flying spot.

Another object of the present invention is to provide an improved scanning device and method for imaging with back-scatter radiation beam, which is advantageous in machinablity and working reliability of the device.

In accordance with an aspect of the present invention, there is provided a scanning device for back-scatter imaging with a radiation beam, comprising: a radiation source; a fixed shield plate and a rotatable shield body respectively disposed between the radiation source and a object to be scanned, wherein the fixed shield plate is stationary with respect to the radiation source and the rotatable shield body is rotatable with respect to the fixed shield plate, wherein: the fixed shield plate is provided with a ray passing-through region thereon, which allows for a radiation beam from the radiation source to pass through the fixed shield plate, and the rotatable shield body is provided on its sides with a ray incidence region and a ray emergence region, respectively, during scanning by rotating the rotatable shield body, the ray passing-through region of the fixed shield plate continually intersects with the ray incidence region and the ray emergence region of the rotatable shield body to generate collimated holes for scanning. The ray passing-through region of the fixed shied plate is a rectilinear slit, the rotatable shield body is a cylinder, and the ray incidence and emergence regions are configured to be a series of small discrete holes disposed along a spiral line, respectively.

Preferably, the fixed shield plate is disposed between the radiation source and the rotatable shield body.

In one embodiment, the scanning device for back-scatter imagining with a radiation beam further comprises: a control device, to control a scanning speed of the radiation beam by controlling a rotational speed of the rotatable shield body and to determine an emergence direction of the radiation beam by detecting a rotational angle of the rotatable shield body.

In one embodiment, the rotatable shield body comprises a plurality of sleeves nested inside and outside each other, wherein an outmost sleeve and an innermost sleeve are made of a material having a certain rigidity and hardness respectively, and at least one middle sleeve is disposed between the outmost sleeve and innermost sleeve and made of a radiation shielding material.

Specifically, the plurality of sleeves are three sleeves, wherein the outmost and innermost sleeves are respectively made of aluminium or steel material, and a middle sleeve is disposed between the outmost and innermost sleeves and made of lead, lead-antimony alloy or tungsten.

Alternatively, the small discrete holes are in a circular, square or ellipse shape.

In the above technical solutions, shape and size of the collimated holes for scanning at different positions can be controlled by controlling shape and size of the series of small discrete holes in the rotatable shield body at different positions, so as to control shape and size of the radiation beam passing through the collimated holes for scanning and appearing on the object to be scanned.

Preferably, a rotatable axis of the rotatable shield body is located in a plane defined by the radiation source and the rectilinear slit in the fixed shield plate.

In accordance with another aspect of the present invention, there is provided a scanning method of back-scatter imaging with a radiation beam, comprising the steps of: providing a radiation source to emit a radiation beam; disposing a fixed shield plate and a rotatable shield body respectively between the radiation source and a object to be scanned, wherein the fixed shield plate is stationary with respect to the radiation source, and the rotatable shield body is rotatable with respect to the fixed shield plate, the fixed shield plate is provided with a ray passing-through region to allow for the radiation beam from the radiation source to pass through the fixed shield plate, a ray incidence region and a ray emergence region are disposed on the rotatable shield body respectively; and rotating the rotatable shield body so that the ray passing-through region of the fixed shield plate continuously intersects with the ray incidence and emergence regions of the rotatable shield body, to generate collimated holes for scanning, wherein the ray passing-through region of the fixed shield plate is a rectilinear slit, the rotatable shield body is a cylinder, the ray incidence and emergence regions are configured to be a series of small discrete holes disposed along a spiral line respectively.

Preferably, the scanning method for the back-scatter imaging with a radiation beam further comprises the step of: controlling a scanning speed of the radiation beam by controlling a rotational speed of the rotatable shield body, and determining an emergence direction of the radiation beam by detecting a rotatable angle of the rotatable shield body.

The above non-specific embodiments of the present invention at least have at least one or more aspects of the advantages and effects:

1. The present invention provides a scanning device incorporating a novel "flying spot" forming structure and the method thereof, which simplifies the scanning structure for back-scatter while obtaining a good shielding effect.

2. In one embodiment, the scanning mechanism and method of the present invention can achieve a controllable scanning of a target object, and sample the target object as required. Accordingly, the image obtained by the scanning device or method of back-scatter imaging with a radiation beam proves to be satisfactory. For example, the scanning mechanism and method of the present invention can scan the target object in a uniform velocity, sample the target object conveniently and uniformly. Consequently, the image obtained by means of the back-scatter scanning device and method does not have a longitudinal compressive deformation.

3. In addition, in the present invention, when rotating the ray scanning sector to perform a second dimensional scan, it would not change an angular momentum direction of the rotatable shield body, since the ray scanning sector and the rotatable shield body can perform rotational movement in a same plane. Therefore, it is not necessary to overcome rotational inertia of the rotatable shield body, and thus is easy to achieve the second dimensional scan through rotating the ray scanning sector.

4. Because in the present invention, the ray incidence and emergence regions are configured to be a series of small discrete holes disposed along a spiral line respectively, the shape and size of the collimated holes for scanning can be effectively controlled by controlling the shape and size of the small discrete holes, so as to provide a uniform flying spot.

5. Moreover, taking into consideration of the problems about the existing production process, the scanning mechanism of the present invention employs the nested sleeve structure. This reduces the weight of the scanning mechanism and resolves the problem of shielding radiation/ray. In the present invention, the ray passing-through region is formed by drilling into the cylinder. In contrast, the spiral slit is formed by machining on the cylinder in the prior art, which turned out to be very cumbersome and costly. Therefore, the present invention is advantageous in significantly improving machinablity of the scanning device.

6. Further, instead of machining a spiral slit on the cylinder, a series of small discontinuous holes are formed on the cylinder. Accordingly, the image obtained through scanning shows that the light spots finally formed on the object to be scanned become interrupted sampling rather than continuous sampling, which in a certain degree alleviates the radiation dose absorbed the object to be detected.

7. Additionally, since in the present invention the radiation source is not disposed inside of the rotatable shield body, the scanning mechanism is assembled together by mating the mechanical interface on the mass-produced X-ray machine. As such, the scanning device has a compact configuration and needs not to redesign the shield body of the X-ray machine, thereby greatly reducing the cost of the scanning device.

DETAILED DESCRIPTION OF THE EMBODIMENTS

Figure 1:
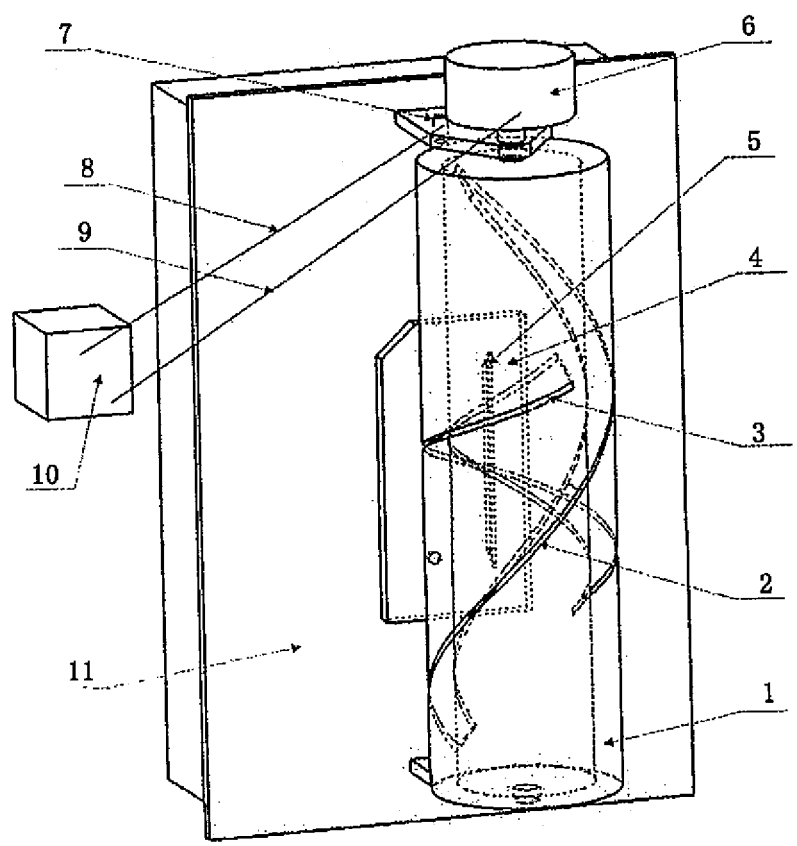
FIG. 1 is a schematic structure view of a scanning device for back-scatter according to an embodiment of the present invention.

Preferred embodiments of the present invention will be described hereinafter in detail with reference to the attached drawings, wherein the like reference numerals refer to the like elements throughout the specification. The present invention may, however, be embodied in many different forms and should not be construed as being limited to the embodiments set forth herein; rather, these embodiments are provided so that the present disclosure will be thorough and complete, and will fully convey the concept of the invention to those skilled in the art.

Figure 2:
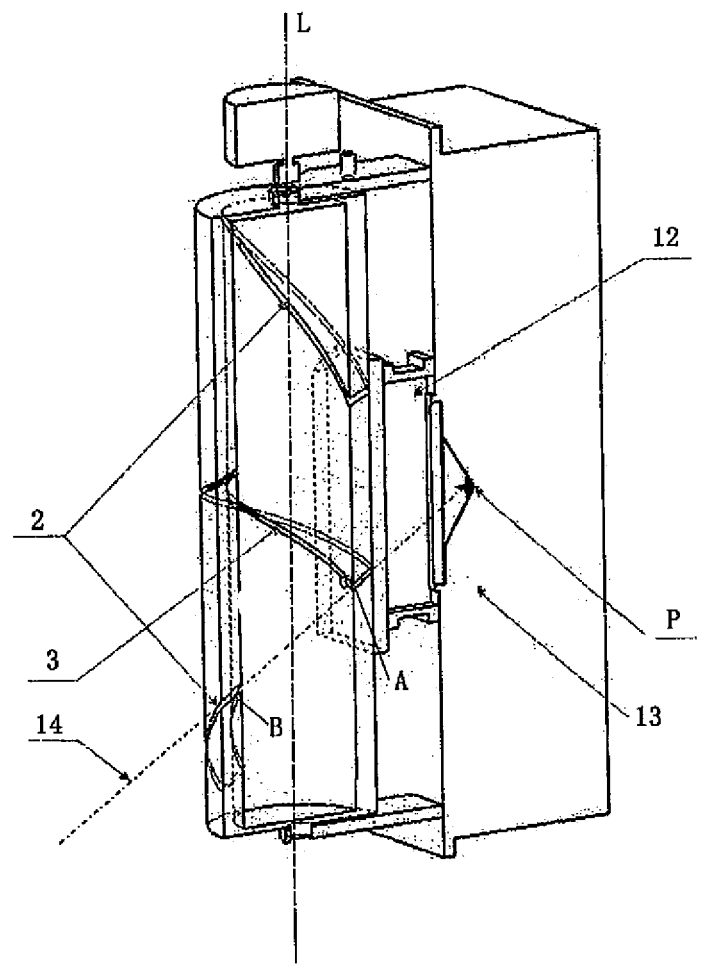
FIG. 2 is a cross-sectional view showing the scanning device for back-scatter in the FIG. 1.
Figure 3:
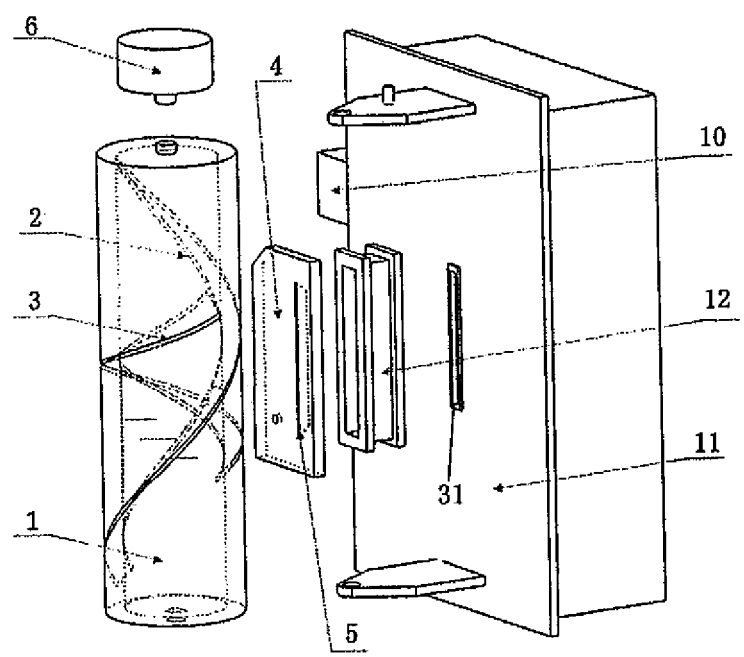
FIG. 3 is an exploded prospective view showing a relationship between a composition and a position of the scanning device for back-scatter in the FIG. 1.
Figure 4:
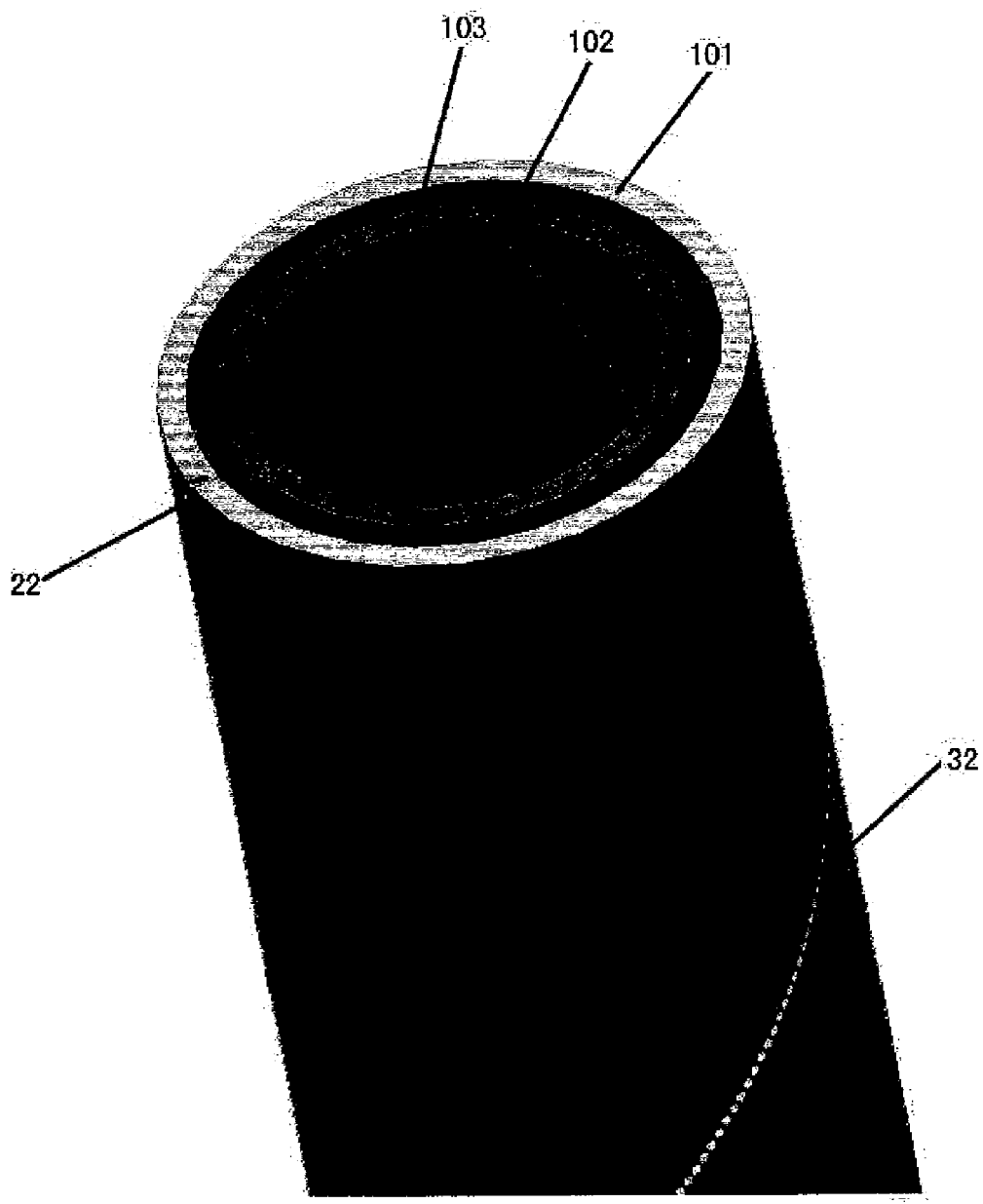
FIG. 4 is a schematic view showing a composition and a structure of a rotatable shield body in the scanning device for back-scatter in the FIGS. 1-3.
Figure 5:
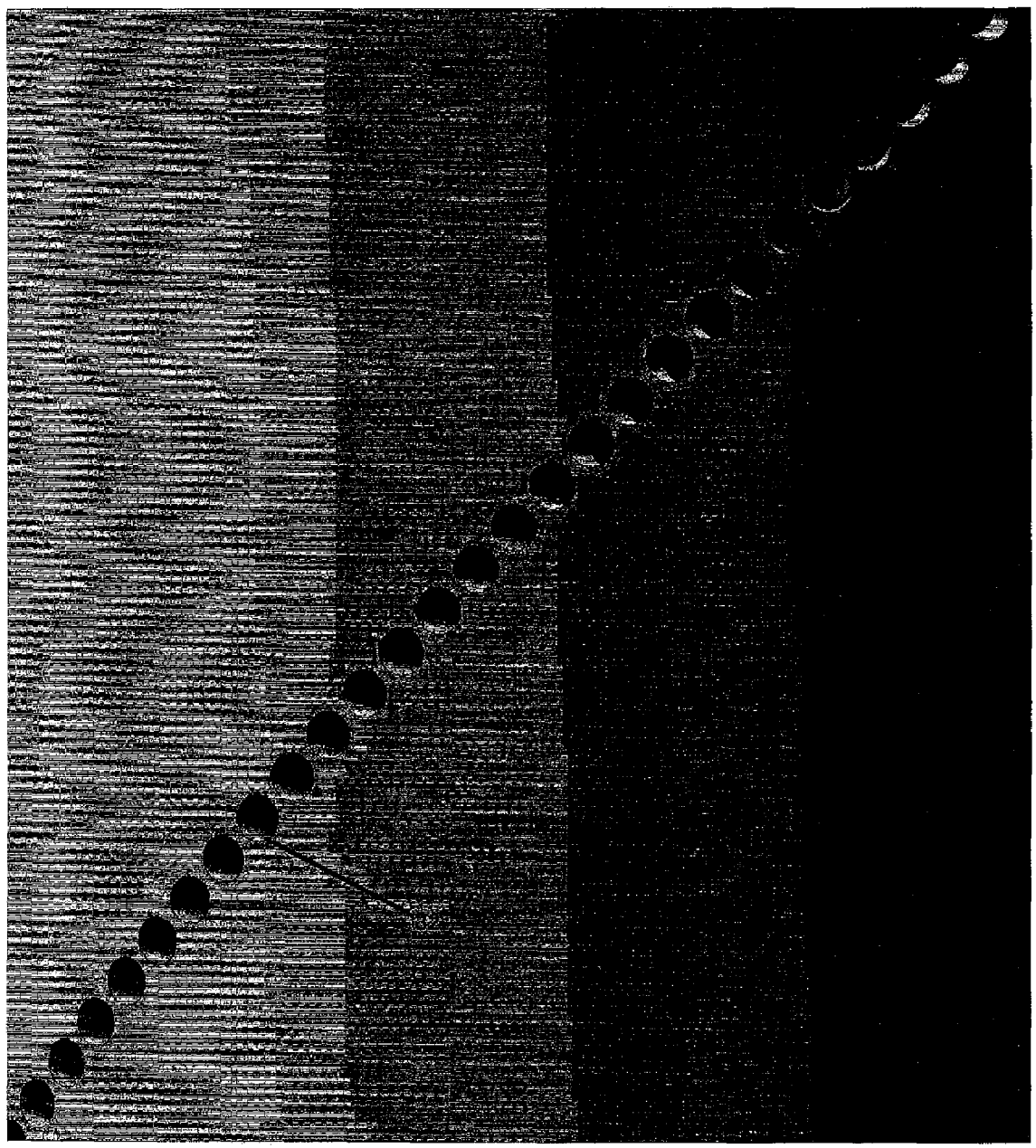
FIG. 5 is an enlarged schematic view showing shape of small holes in ray incidence and emergence regions of the scanning device for back-scatter in the FIGS. 1-3.

Referring to FIGS. 1-3, it illustrates a scanning device of back-scatter imaging with a radiation beam in accordance with one specific embodiment of the present invention. It includes a radiation source 13, for example a X-ray machine; and a fixed shield plate 4 and a rotatable shield body 1 respectively disposed between the radiation source 13 and a object to be scanned (not shown in the figure, for example at a left side of the FIG. 2), wherein the fixed shield plate 4 is stationary with respect to the radiation source 13, and the rotatable shield body 1 is rotatable with respect to the fixed shield plate 4. Further, the fixed shield plate 4 is provided thereon with a passing-through region such as a longitudinal slit 5 in the FIGS. 1-3, which allows for a radiation beam (i.e., ray) from the radiation source 13 to pass through the fixed shield plate 4. A ray incidence region 3, such as a series of small discrete holes 32 disposed along a spiral line of FIGS. 1-5, and a ray emergence region 2, such as a series of small discrete holes 22 disposed along the spiral line of the FIGS. 1-5, are arranged on the rotatable shield body 1 respectively. During the scanning operation through rotating the rotatable shield body 1, the ray passing-through region 5 of the fixed shield plate 4 continuously intersects with the ray incidence region 3 and the ray emergence region 2 of the rotatable shield body 1 to generate collimated holes i.e. flying spots, for scanning. In the above embodiment, the fixed shield plate 4 is disposed between the radiation source 13 and the rotatable shield body 1.

In the above embodiment of the present invention, a ray generator includes an enclosure 11 of the ray generator and a radiation source 13 housed in the enclosure 11. With the above construction, the radiation source 13 can be X-ray machine, λ-ray source or isotope ray source, and the like. As shown in FIGS. 1 and 3, the enclosure 11 of the ray generator in one specific embodiment is generally in the shape of a rectangular box, and it is provided with a collimating slit 31 which enables radiation ray emitted from the radiation source 13 to emerge out of the enclosure 11. The radiation beam 14 emitted from a target point P of the radiation source 13 passes through the collimating slit 31 to form a ray sector, and through the passing-through region of the fixed shield plate 4 (for example the longitudinal slit 5 of the FIGS. 1-3). Further, it passes through the ray incidence region 3 of the rotational shield body 1, such as a series of small discrete holes 32 disposed along a spiral line of the FIGS. 1-5, and the ray emergence region 2, such as a series of small discrete holes 22 disposed along the spiral line of the FIGS. 1-5. By adjusting a relative relationship among the longitudinal slit 5 of the fixed shield plate 4 and the small discrete holes 32 and 22 of the rotatable shield body 1, the ray passing-through region 5 of the fixed shield plate 4 continuously intersects with the small discrete holes 32 in the ray incidence region 3 and the small discrete holes 22 in the ray emergence region 2 of the rotatable shield body 1 during the rotatable scanning of the rotatable shield body 1, thus generating collimated holes for scanning. In other words, the small discrete holes 32 in the ray incidence region 3 and the small discrete holes 22 in the ray emergence region 2 of the rotatable shield body 1 as well as the longitudinal and narrow slit 5 of the fixed shield plate cooperate together to form a ray collimated holes. Alternatively, referring to the FIG. 5, the small discrete holes 32 and 22 are in a circular, square or ellipse shape, preferably being circular.

As shown in FIGS. 1-3, the ray passing-through region 5 of the fixed shield plate 4 is a rectilinear slit (i.e., in a straight line), the rotatable shield body 1 is a cylinder, and the ray incidence and emergence regions 3 and 2 are configured to be, a series of small discrete holes 32 and 22 disposed along a spiral line, respectively. Specifically, referring to FIG. 2, any small discrete hole in the ray incidence and emergence regions 3 and 2 as shown therein (for example points A and B), performs a uniform and circumferential motion along a cylindrical plane of the rotatable shield body 1, and synchronically makes a rectilinear motion in accordance with a certain speed gradient along a radial direction of the rotatable shield body 1, thereby generating a certain cylindrical spiral line. In one specific embodiment, any point in the ray incidence and emergence regions 3 and 2 as shown therein (for example points A and B), perform a uniform and circumferential motion along the cylindrical plane of the rotatable shield body 1, and synchronically makes a uniform and rectilinear motion along a radial direction of the rotatable shield body 1, thereby generating a uniform and cylindrical spiral line.

Referring to FIG. 2, when determining the target point P of the radiation source 13 and the point A of the ray incidence region 3, it is possible to ascertain an emergence point B on the ray emergence region 2 by a radiation beam 14 which is formed by connecting the target point P of the radiation source 13 to the incidence point A of the ray incidence region 3.

Since the ray incidence and emergence regions 3 and 2 are set in the shape of an uniform and circumferential spiral line, when the rotatable shield body 1 uniformly rotates, positions of the ray collimated holes move with the rotation of the rotatable shield body 1, and thus the beam of emergence ray 14 moves. As a result the collimated holes for scanning continuously and uniformly move along the rectilinear slit 5.

Although in the above embodiment the ray incidence and emergence regions 3 and 2 are set in the shape of the uniform and circumferential spiral line, the present invention is not limited to this, for example, the ray incidence and emergence regions 3 and 2 can be set in the shape of the specific spiral line as described above. Namely, it performs a uniform and circumferential motion along the cylindrical plane of the rotatable shield body 1, and synchronically makes a rectilinear motion in accordance with a certain speed gradient along the radial direction of the rotatable shield body 1, thereby forming a specific and cylindrical spiral line. Accordingly, when the rotatable shield body 1 uniformly rotates, positions of the ray collimated holes move with the rotation of the rotatable shield body 1, thus the beam of emergence ray 14 moves, so that the collimated holes for scanning move along the rectilinear slit 5 in accordance with a predefined speed gradient. Thus, the scanning device of the present invention can achieve a controllable scanning of a target object, sample the target object in accordance with specific requirements, and enable satisfactory image by back-scatter scanning, thereby improving quality and resolution of the back-scatter imaging, enhancing precision and efficiency of the back-scatter detection, and satisfying different requirements.

Further, the scanning device includes a driving device 6 to drive and rotate the rotatable shield body 1, for example a speed regulating motor, and the like. Referring to the FIG. 4, in one embodiment the rotatable shied body 1 includes a plurality of sleeves nested inside and outside each other. Specifically, the outermost and innermost sleeves are formed of a material having a certain rigidity and hardness respectively, and at least one middle sleeve is disposed between the outermost and innermost sleeves and made of a radiation shielding material. In one specific embodiment, the rotatable shield body 1 as shown in the FIG. 4 includes three sleeves 101, 102, and 103 (not labelled as therein). Specifically, the outermost and innermost sleeves 101 and 102 are formed of aluminium or steel material respectively, and one middle sleeve 102 is disposed between the outermost and innermost sleeves and made of lead, lead-antimony alloy or tungsten.

Specifically, in the above embodiments, the scanning device (see FIG. 1) also includes a rotatable encoding disc reading-out device 7 to detect rotatable positions of the rotatable shield body 1, and an encoding disc reading-out signal line 8 to input the detected information about the rotatable positions of the rotatable shield body 1 into a control device 10. Since the rotatable positions of the rotatable shield body 1 determine the positions of the collimated holes for scanning. With the above configuration, it is possible to detect the positions formed by the collimated holes for scanning. As shown in the FIG. 1, the control device 10 can further control the rotation of the rotatable shield body 1 by connecting a motor drive line 9 and a drive motor 6. A scan speed of the radiation beam can be controlled by controlling the rotatable speed of the rotatable shield body 1, while the emergence direction of the radiation beam can be obtained by detecting a rotatable angle of the rotatable shield body 1. Referring to the FIG. 2, in one embodiment, a rotatable axis L of the rotatable shield body 1 can be located in a plane defined by the radiation source 13 and the rectilinear slit 5 in the fixed shield plate 4.

In the above embodiments, the shape and size of the collimated holes for scanning at different positions can be controlled by controlling the shape and size of the series of small discrete holes 32 and 22 in the rotatable shied body 1 at different positions, so that it is possible to control the shape and size of the radiation beam passing through the collimated holes for scanning and impinging on the object to be detected. For example, the size, such as the diameter of the small discrete holes 32 and 22 in the ray incidence and emergence regions 3 and 2 located at both longitudinal ends of the rotatable shield body 1 can be smaller than that of the small discrete holes located at longitudinal and central positions thereof, while the collimated holes for scanning formed by the small discrete holes 32 and 22 located at both longitudinal ends of the rotatable shield body 1 are at a certain angle with respect to the collimated holes for scanning located at the longitudinal and central positions thereof. With the above structure, it can ensure that the ray collimated holes always align to the target point and keep unblocked, and the sectional shape of the radiation beam which passes through the collimated holes for scanning and impinges on the object to be scanned, when being at different positions, keeps to be constant. However, the present invention is not limited to this. For example, the shape and size of the collimated holes for scanning at different positions can be controlled by controlling small discrete holes 32 and 22 of the ray incidence and emergence regions 3 and 2 in the rotatable shield body 1, and accordingly, the shape and size of the radiation beam passing through the collimated holes for scanning and impinging on the object to be scanned can be controlled so as to adapt to the different scanning demands.

With reference to the FIG. 3, the enclosure 11 of the ray generator is used to ensure shielding the ray by connecting the shield sleeve 12 and the fixed shield plate 4. It can be seen from the above configuration that the radiation source 13 is arranged in the interior of the enclosure 11 of the ray generator, rather than in the interior of the rotatable shield body 1, and the scanning mechanism can be achieved by mating with the shield sleeve 12 in a mass-produced X-ray machine as the mechanical interface. As such, the structure of the scanning device becomes compact, avoiding redesign of the shield body of the X-ray machine, thereby saving the cost thereof.

The scanning method of back-scatter imaging with a radiation beam in accordance with the present invention can be briefly explained below taken in combination with the accompanying drawings.

Referring to the FIGS. 1-3, the scanning method of back-scatter imaging with a radiation beam in accordance with one specific embodiment of the present invention, includes the following steps: providing a radiation source 13 to emit a radiation beam 14; disposing a fixed shield plate 4 and a rotatable shield body 1 respectively between the radiation source 13 and a object to be scanned, wherein the fixed shield plate 4 is stationary with respect to the radiation source, and the rotatable shield body 1 is rotatable with respect to the fixed shield plate 4, the fixed shield plate 4 is provided with a ray passing-through region to allow for the radiation beam 14 from the radiation source 13 to pass through the fixed shield plate 4, a ray incidence region 3 and a ray emergence region 2 are disposed on the rotatable shield body 1 respectively; and rotating the rotatable shield body 1 so that the ray passing-through region 5 of the fixed shield plate 4 continuously intersects with the ray incidence and emergence regions 3 and 2 of the rotatable shield body 1, to generate collimated holes for scanning, i.e. the flying spot. The ray passing-through region of the fixed shield plate 4 is a rectilinear slit 5, the rotatable shield body 1 is a cylinder, the ray incidence and emergence regions 3 and 2 are configured to be a series of small discrete holes 32 and 22 disposed along a spiral line respectively.

During the scanning process as described above, when the rotatable shield body 1 uniformly rotates, the collimated holes for scanning continuously move along the rectilinear slit 5 at a controllable speed.

Referring to the FIG. 1, during the scanning process, the control device 10 can read out the current state of the rotatable shield body 1 by the rotatable encoding disc reading-out device 7 and encoding disc reading-out signal line 8, to further determine the current position of the ray collimated hole. Based on the positional detection of the collimated holes for scanning, the emergence direction of the radiation beam 14 can be further obtained. Moreover, the collimated holes for scanning are further set so that it maintains predetermined shape with respect to the radiation source 13, and the sectional shape of the radiation beam 14 passing through the collimated holes and impinging on the object to be scanned keeps a predetermined shape, thus satisfying different demands on the scanning operation.

Although some embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What the claims is:

1. A scanning device of back-scatter imaging with a radiation beam, comprising:
   a radiation source;
   a fixed shield plate and a rotatable shield body disposed between the radiation source and an object to be scanned respectively, wherein the fixed shield plate is stationary with respect to the radiation source and the rotatable shield body is rotatable with respect to the fixed shield plate;
   a control device, to control a scanning speed of the radiation beam by controlling a rotational speed of the rotatable shield body and to obtain an emergence direction of the radiation beam by detecting a rotational angle of the rotatable shield body, wherein:
   the fixed shield plate is provided with a ray passing-through region thereon, which allows for a radiation beam from the radiation source to pass through the fixed shield plate,
   a ray incidence region and a ray emergence region are arranged on the rotatable shield body respectively, during the rotatable scanning of the rotatable shield body, the ray passing-through region of the fixed shield plate continuously intersects with the ray incidence region and the ray emergence region of the rotatable shield body to generate collimated holes for scanning, characterized in that:
   the ray passing-through region of the fixed shield plate is a rectilinear slit, the rotatable shield body is a cylinder, and the ray incidence and emergence regions are configured to be a series of small discrete holes disposed along a spiral line respectively.

2. The scanning device as claimed in claim 1, characterized in that:
   the fixed shield plate is disposed between the radiation source and the rotatable shield body.

3. The scanning device as claimed in claim 2, characterized in that:
   a rotatable axis of the rotatable shield body is located in a plane defined by the radiation source and the rectilinear slit in the fixed shield plate.

4. The scanning device as claimed in claim 1, characterized in that:
   the rotatable shield body comprises a plurality of sleeves nested inside and outside each other, wherein an outmost sleeve and an innermost sleeve are made of a material having a certain rigidity and hardness respectively, and at least one middle sleeve is disposed between the outmost sleeve and innermost sleeve and made of a radiation shielding material.

5. The scanning device as claimed in claim 4, characterized in that:
   the plurality of sleeves include three sleeves, wherein the outmost and innermost sleeves are made of aluminium or steel material respectively, and a middle sleeve is disposed between the outmost and innermost sleeves and made of lead, lead-antimony alloy or tungsten.

6. The scanning device as claimed in claim 5, characterized in that:
   the small discrete holes are in a circular, square or ellipse shape.

7. A scanning device as claimed in claim 6, characterized in that:
   shape and size of the collimated holes for scanning at different positions can be controlled by controlling shape and size of the series of small discrete holes in the rotatable shield body at different positions, so as to control shape and size of the radiation beam passing through the collimated holes for scanning and impinging on the object to be scanned.

8. A scanning method for back-scatter imaging with a radiation beam, comprising the steps of:
   providing a radiation source to emit a radiation beam;
   disposing a fixed shield plate and a rotatable shield body between the radiation source and an object to be scanned respectively, wherein the fixed shield plate is stationary with respect to the radiation source, and the rotatable shield body is rotatable with respect to the fixed shield plate, the fixed shield plate is provided with a ray passing-through region to allow for the radiation beam from the radiation source to pass through the fixed shield plate, a ray incidence region and a ray emergence region are respectively disposed on the rotatable shield body;
   rotating the rotatable shield body so that the ray passing-through region of the fixed shield plate continuously intersects with the ray incidence and emergence regions of the rotatable shield body, to generate collimated holes for scanning; and
   controlling a scanning speed of the radiation beam by controlling a rotational speed of the rotatable shield body and obtaining an emergence direction of the radiation beam by detecting a rotational angle of rotatable shield body;
   characterized in that:
   the ray passing-through region of the fixed shield plate is a rectilinear slit, the rotatable shield body is a cylinder, the ray incidence and emergence regions are configured to be a series of small discrete holes disposed along a spiral line respectively.

9. The scanning method as claimed in claim 8, characterized in that:
   the fixed shield plate is disposed between the radiation source and the rotatable shield body.

10. The scanning method as claimed in claim 8, characterized in that:
    shape and size of the collimated holes for scanning at different positions can be controlled by controlling shape and size of the series of small discrete holes in the rotatable shield body at different positions, so as to control shape and size of the radiation beam passing through the collimated holes for scanning and impinging on the object to be detected.

* * * * *